US009649453B2

(12) United States Patent
Roberts et al.

(10) Patent No.: US 9,649,453 B2
(45) Date of Patent: May 16, 2017

(54) SAFETY DEVICES (75) Inventors: Gareth Roberts, Wrexham (GB); Chris Ward, Denbighshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 230 days.

(21) Appl. No.: 13/880,518

(22) PCT Filed: Oct. 25, 2011

(86) PCT No.: PCT/EP2011/068594
§ 371 (c)(1),
(2), (4) Date: Apr. 19, 2013

(87) PCT Pub. No.: WO2012/055839
PCT Pub. Date: May 3, 2012

(65) Prior Publication Data
US 2013/0204200 A1 Aug. 8, 2013

(30) Foreign Application Priority Data

Oct. 25, 2010 (EP) .................................... 10188658

(51) Int. Cl.
*A61M 5/32* (2006.01)
(52) U.S. Cl.
CPC .......... *A61M 5/3257* (2013.01); *A61M 5/326* (2013.01); *A61M 5/3272* (2013.01); *A61M 2005/3267* (2013.01)
(58) Field of Classification Search
CPC ........ A61M 2005/3267; A61M 5/3257; A61M 5/326; A61M 5/3272; A61M 2005/3268; A61M 5/3271; A61M 2005/3263; A61M 5/3245; A61M 5/3243; A61M 2005/3256
See application file for complete search history.

(56) References Cited

U.S. PATENT DOCUMENTS

| 5,279,581 A | | 1/1994 | Firth et al. |
| 5,584,818 A | * | 12/1996 | Morrison ...................... 604/197 |
| 6,099,504 A | * | 8/2000 | Gross .................. A61M 5/2046 |
| | | | 604/140 |

(Continued)

FOREIGN PATENT DOCUMENTS

| JP | 2008-526340 | 7/2008 |
| JP | K2008-220949 | 9/2008 |

(Continued)

OTHER PUBLICATIONS

Form PCT/IPEA/416, Notification of Transmittal of the International Preliminary Report on Patentability.

(Continued)

Primary Examiner — Rebecca E Eisenberg
Assistant Examiner — Weng Lee
(74) Attorney, Agent, or Firm — Fish & Richardson P.C.

(57) ABSTRACT

According to the invention, a safety device for a pre-filled syringe comprises a hollow support body for retaining the pre-filled syringe therein, a hollow needle shield and a spring means made from a resilient plastics material. The needle shield is telescoped with the support body and the spring means biases the needle shield in a distal direction.

14 Claims, 5 Drawing Sheets

(56) References Cited

U.S. PATENT DOCUMENTS

| | | | |
|---|---|---|---|
| 7,566,324 B2* | 7/2009 | Hommann | A61M 5/3205 604/197 |
| 7,799,002 B2* | 9/2010 | Dillard, III | A61M 5/3257 267/71 |
| 2003/0120218 A1* | 6/2003 | Asbaghi | A61M 5/3202 604/198 |
| 2004/0127857 A1* | 7/2004 | Shemesh et al. | 604/198 |
| 2006/0229569 A1* | 10/2006 | Lavi | A61M 5/326 604/197 |
| 2008/0228147 A1 | 9/2008 | David-Hegerich et al. | |
| 2009/0326477 A1* | 12/2009 | Liversidge | 604/198 |

FOREIGN PATENT DOCUMENTS

| | | |
|---|---|---|
| WO | 2009048737 A1 | 4/2009 |
| WO | WO 2010/019936 | 2/2010 |

OTHER PUBLICATIONS

International Preliminary Report on Patentability in International Application No. PCT/EP2011/068594, dated Dec. 20, 2012, 21 pages.

International Search Report and Written Opinion in International Application No. PCT/EP2011/068594, dated May 3, 2012, 14 pages.

* cited by examiner

SAFETY DEVICES

CROSS REFERENCE TO RELATED APPLICATIONS

The present application is a U.S. National Phase Application pursuant to 35 U.S.C. §371 of International Application No. PCT/EP2011/068594 filed Oct. 25, 2011, which claims priority to European Patent Application No. 10188658.8 filed Oct. 25, 2010. The entire disclosure contents of these applications are herewith incorporated by reference into the present application.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solve the object of providing needle safety by arranging the pre-filled syringe movable relative to a body, whereas the pre-filled syringe is retracted into the body after the injection.

Other safety devices are known from WO 2009/048737 A1 and US 2009/326477 A1.

SUMMARY

It is an object of the present invention to provide an improved safety device for a pre-filled syringe.

In certain aspects, an injection device including a pre-filled syringe that is safe to handle and in particular prevents accidental needle stick injuries is provided.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a hollow support body for retaining the pre-filled syringe therein, a hollow needle shield and a spring means made from a resilient plastics material and arranged between the needle shield and the support body. The needle shield is telescoped with the support body and the spring means biases the needle shield in a distal direction.

The needle shield slides relative to the support body in a telescopic manner parallel to a central axis of the safety device. The spring means biases the needle shield in the distal direction to prevent accidental needle stick injuries before, during and after an injection. The safety device providing needle safety for the pre-filled syringe retained in the support body is entirely made from plastics materials. As plastics materials like polymers or elastomers are inexpensive and the safety device comprises only a low number of parts, the safety device can be economically produced in high quantities. The safety device is thus very well suited to be used in combination with disposable pre-filled syringes and is disposed together with the pre-filled syringe after a single injection has been performed.

The needle shield comprises an axial length that substantially corresponds to maximal spring deflection of a spring means arranged within the needle shield. The axial length of the needle shield is adapted in a way, so that the spring means is retained within the hollow interior of the needle shield throughout the injection. The spring means is protected from exterior effects ensuring a reliable use of the safety device.

The spring means comprises a plurality of generally L-shaped resilient spring leaves corresponding to the number of first side walls of the needle shield. The spring leaves are in a relaxed state when the needle shield is in an initial position, wherein the needle shield extends from the support body in the distal direction. The spring leaves bias the needle shield in the distal direction and are bent and get stressed when the needle shield moves from the initial to a retracted position.

According to a possible embodiment of the invention, the needle shield comprises a plurality of substantially planar or convex first side walls. The safety device is designed to differ in its outer appearance from typical designs of safety devices for pre-filled syringes. The safety device according to the present invention has a design that is in general not associated by a typical user with the unpleasant act of receiving an injection. The design of the safety device thus alleviates a possible fear of receiving an injection. This is particularly useful in the context of self-administered injections, as a fear of needles or injections might keep the patient from performing the injection properly.

In a possible embodiment of the invention, all first side walls of the needle shield have the same first width. Thus, the needle shield substantially comprises a cross-section of a regular polygon. The discrete symmetrical shape of the needle shield advantageously supports the use of the plurality of spring leaves arranged within the needle shield.

The spring leaves are arranged within the needle shield in a manner, so that the leaf springs are oriented relative to each other at an angle. Each spring leaf is arranged adjacent to one of the first side walls of the needle shield in a plane substantially parallel the first side wall of the needle shield. The design of the spring leaves and the arrangement of the spring leaves are adapted to the polygonal, e.g. a triangular design of the support body.

A double-walled outer body telescopes with respect to the support body during the injection. The outer body comprises a plurality of substantially planar or convex outer side walls. Each outer side wall is arranged parallel to one of the first side walls of the needle shield. The outer body telescopes with respect to the needle shield during the injection and is substantially received within the needle shield at the end of an injection stroke. The safety device comprises compact dimension to spare material, so that the safety device can be cost-effectively produced.

According to possible embodiment of the invention, the spring leaves are arranged within the needle shield in a manner, so that the leaf springs are oriented relative to each other at an angle. Each spring leaf is arranged adjacent to one of the first side walls of the needle shield in a plane substantially parallel to the first side wall of the needle shield. The design of the spring leaves and the arrangement of the spring leaves are adapted to the polygonal design of the needle shield.

The spring leaf is operably connected to a distal end wall of the needle shield and to a distal shroud. The spring leaf biases the distal end wall and the distal shroud away from each other. In one possible embodiment of the invention, the spring leaf bears against a distal end wall of the needle shield in the distal direction and against a distal shroud of the support body in a proximal direction.

According to a possible embodiment of the invention, the support body comprises a plurality of substantially planar or convex second side walls. An inner sleeve of the needle shield comprises a plurality of substantially planar or convex third side walls, wherein each third side wall is arranged parallel to one of the second side walls. The inner sleeve is substantially received within the support body when the needle shield telescopes with respect to the support body. The safety device has a shape that avoids a continuous rotational symmetric layout typically found in tubular safety device designs. A relative rotation between the needle shield and the support body is prevented when these parts are slid relative to each other. The relative rotation of needle shield and support body might be uncomfortable for a patient receiving an injection, in particular as the needle shield abuts the skin-surface of the patient during the injection. The safety device thus allows for a safe and convenient injection of a medication.

According to a possible embodiment of the invention, all second side walls of the support body have the same second width and all third side walls of the inner sleeve have the same third width. The third width is adapted to the second width, so that the inner sleeve may be retained within the support body of the safety device. The parts constituting the safety device have substantially cylindrical designs with basis planes in the shape of regular polygons. The safety device provides a design to avoid possible patient's fear of needles.

In a possible embodiment of the invention, at least one flexible arm is formed to one of the third side walls of the inner sleeve. The flexible arm is deflectable in a lateral direction perpendicular to the central axis and comprises a guide pin that protrudes in a radial direction. The guide pin is moved within and along a guide track when the needle shield is slid relative to the support body to cover and/or to expose in particular a hypodermic needle of a pre-filled syringe inserted into the support body of the safety device. The movement of the needle shield is controlled by the guide pin moving between various positions within the guide track. The interplay of the deflectable flexible arm with the separating wall allows a guidance of the guide pin along the guide track that avoids a relative rotation of any external parts like the needle shield and the support body.

According to the same embodiment, a guide track is formed into at least one of the second side walls of the support body. The guide pin protrudes into and interacts with the guide track. The interaction of the guide pin with the guide track retains the needle shield in the initial position and in an advanced position. Furthermore, the guide pin interacting with the guide track guides the movement of the needle shield between the initial position, the retracted position and the advanced position According to another possible embodiment, the double-walled outer body is slidably arranged with respect to the support body. The outer body comprises a plurality of inner side walls. Each inner side wall is arranged parallel to one of the second side walls of the support body. The inner side wall apposes the second side wall when the outer body is moved with respect to the inner body, whereby a relative rotation of outer body and support body is prevented. Thus, the outer body is movable with respect to the support body in a linear motion to perform the injection stroke.

The number and shape of the inner side walls may differ from the number and shape of the outer side walls. The number and shape of inner side walls corresponds to the second side walls the support body. For example, the support body may be formed by three substantially planar second side walls. Correspondingly, the outer body has three substantially planar inner side walls. As the support body is received in the hollow space limited by the inner side walls when outer body is slid with respect to the support body in the distal direction, a relative rotation of outer body and support body is prevented. The number and shape of the outer side walls corresponds to the number and shape of the first side walls of needle shield. In particular, a design of the outer body and of the needle shield may be adapted to provide an ergonomic or tactile support for the user of the safety device. For example, the first side walls and the outer side walls may be arranged to form a needle shield and an outer body with a rectangular cross-section with a cross-section of a regular hexagon.

According to a possible embodiment of the invention, the support body is substantially received within the outer body at the end of an injection stroke, whereby the support body is locked relative to the outer body. The guide pin and the guide track retaining the needle shield in the advanced position is thus kept inaccessible for a user in the inside of the outer body. This prevents a user to tamper with the guide track and the guide pin after a first use of the device, so that a manipulation allowing for a re-use of the safety device is avoided.

An injection device comprises the safety device and a pre-filled syringe. The pre-filled syringe is retained within the support body, so that the hypodermic needle protrudes the support body in a distal direction. The injection device comprising the pre-filled syringe and the safety device combines the aforementioned advantages and avoids inadvertent needle sticks before, during and after an injection delivering the medication beneath the skin of patient.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figures 1, 2A, 2B, 2C:
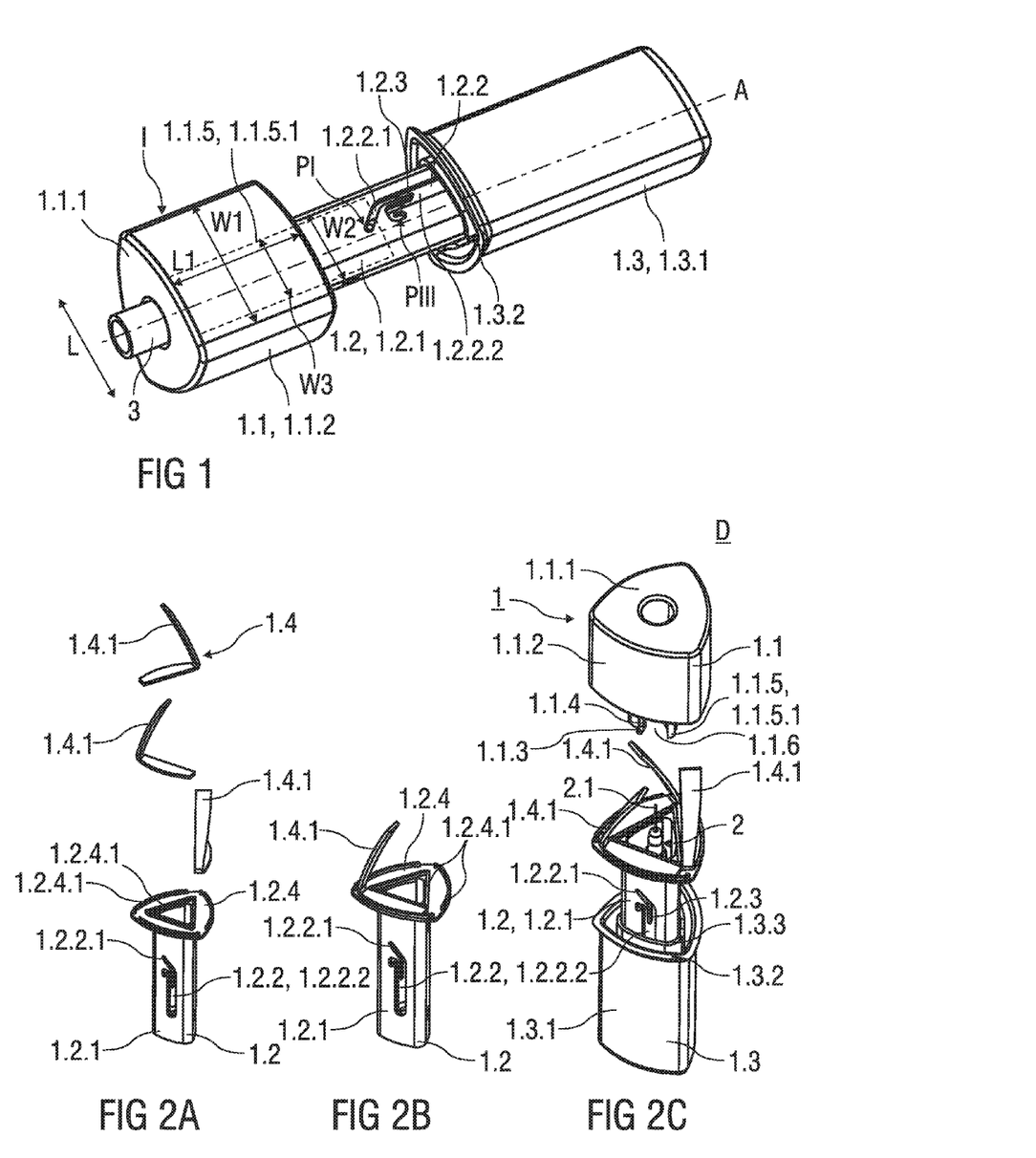
FIG. 1 shows a perspective view of an injection device comprising a safety device and a pre-filled syringe prior to use.
FIGS. 2A to 2C show an exploded view of a support body, a spring means and an injection device.

FIG. 1 shows an injection device D with a safety device 1 for a pre-filled syringe 2 as it would be presented to a user performing an injection. The safety device 1 comprises a hollow needle shield 1.1 that surrounds a hypodermic needle 2.1 of the pre-filled syringe 2 prior to use. The needle shield 1.1 has a substantially equilateral triangular distal end wall 1.1.1 with a central aperture centred on a central axis A of the safety device. The distal end wall 1.1.1 is adapted to be pressed against the skin of a patient. Edges of the distal end wall 1.1.1 that come in contact with the skin of the patient are rounded to avoid injuries.

The needle shield 1.1 comprises three substantially planar and slightly convex first side walls 1.1.2 oriented at an angle of approximately 60 degrees relative to each other. Each of the first side walls 1.1.2 has a first width W1 extending essentially perpendicular to the central axis A.

The needle shield 1.1 is slidable with respect to the support body 1.2. The support body 1.2 comprises three substantially planar and slightly convex second side walls 1.2.1, wherein each second side wall 1.2.1 is arranged parallel to one of the first side walls 1.1.2 of the needle shield 1.1. Prior to use of the safety device 1, the needle shield 1.1 is retained in an initial position I, wherein the needle shield 1.1 axially displaced with respect to the support body 1.2 in a distal direction.

Each second side wall 1.2.1 has a second width W2 extending essentially perpendicular to the central axis A and an axial length L1 extending parallel to the central axis A.

As indicated by the dashed line in FIG. 1, an inner sleeve 1.1.5 is integrated to the needle shield 1.1. A proximal end of the inner sleeve 1.1.5 is received within a distal end of the support body 1.1. The inner sleeve 1.1.5 comprises three slightly convex third side walls 1.1.5.1, wherein each third side wall 1.1.5.1 apposes one of the second side walls 1.2.1 of the support body 1.2. The inner sleeve 1.1.5 slides into the support body 1.2 when the needle shield 1.1 is moved relative to the needle shield 1.1. As the inner sleeve 1.1.5 and the support body 1.2 have a shape that is not rotational symmetric, a relative rotation of the needle shield 1.1 and the support body 1.2 is prevented during the translatory movement of the needle shield 1.1 relative to the support body 1.2. Each third side wall 1.1.5.1 has a width W3.

As illustrated in FIG. 1, all first side walls 1.1.2 of the needle shield 1.1 have the same first width W1, all second side walls 1.2.1 of the support body 1.2 have the same second width W2 and all third side walls 1.1.5.1 of the inner sleeve 1.1.5 have the same third width W3.

The number and shape of the third side walls 1.1.5.1 of the inner sleeve 1.5.1 corresponds to the number and shape of the second side walls 1.2.1 of the support body 1.2.

In alternative embodiments of the invention the support body 1.2 has a cross-section of a polygon and, in particular, a regular polygon with a number of second side walls 1.2.1. For example, the support body may have a cross-section of a regular hexagon and comprise six substantially planar second side walls 1.2.1. The inner sleeve 1.1.5 received within the support body 1.2 apposes the six planar second side walls 1.2.1. Consequently, the inner sleeve 1.1.5 has six substantially planar third side walls 1.1.5.1 that appose the second side walls 1.2.1, so the needle shield 1.1 slides with respect to the support body 1.2 in a linear motion, whereby a relative rotation between support body 1.2 and needle shield 1.1 is avoided.

Figure 3:
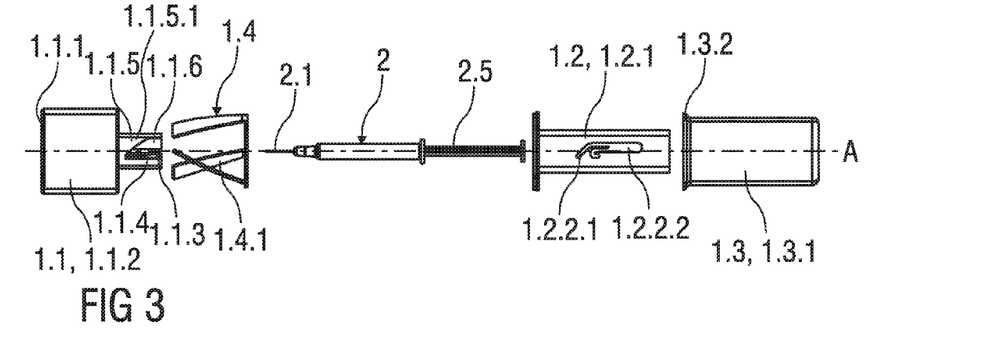
FIG. 3 shows an exploded side view of an injection device.

With cross-reference to the exploded views of FIGS. 2C and 3, it can be seen that a guide pin 1.1.3 is integrally formed to a flexible arm 1.1.4 of the needle shield 1.1. The flexible arm 1.1.4 is formed to the inner sleeve 1.1.5 of the needle shield 1.1 and extends in its rest position essentially parallel to the central axis A of the safety device 1. A trapezoid cut-out 1.1.6 is formed into the needle shield 1.1 adjacent to the flexible arm 1.1.4 to allow for a deflection and pivoting movement of the flexible arm 1.1.4.

As illustrated in FIG. 1, the guide pin 1.1.3 protrudes radial outwards into a guide track 1.2.2 formed into one of the second side walls 1.2.1. Prior to use of the safety device 1, the guide pin 1.1.3 is retained within an inclined section 1.2.2.1 of the guide track 1.2.2 in a start position PI located at a distal end of the guide track 1.2.2. As the flexible arm 1.1.4 is in a so-called rest position, the guide pin 1.1.3 is laterally non-biased in the start position PI. The inclined section 1.2.2.1 is oriented at an acute angle relative to the central axis A of the safety device 1.

The needle shield 1.1 is retained in the initial position I by the guide pin 1.1.3 being retained in the start position PI in the inclined section 1.2.2.1 of the guide track 1.2.2. The needle shield 1.1 is made from an opaque plastics material, so that a hypodermic needle 2.1 of the pre-filled syringe 2 retained within the safety device 1 is hidden from view of the patient before the injection.

Alternatively, the needle shield 1.1 is made from a transparent plastics material, so that a healthcare professional performing the injection may visually confirm the correct placement of the hypodermic needle 2.1 before penetrating the skin of the patient.

The guide pin 1.1.3 is prevented from leaving the start position PI by an interaction of several components of the safety device 1: Upon deflection, the flexible arm 1.1.4 biases the guide pin 1.1.3 in a lateral direction L perpendicular to the central axis A and back towards the start position PI. The guide pin 1.1.3 abuts the distal end of the inclined section 1.2.2.1 in the lateral direction L and in the distal direction.

The guide track 1.2.2 comprises a widened section 1.2.2.2 extending parallel to the central axis A of the safety device 1. A flexible separating wall 1.2.3 extends parallel to the central axis A and into the widened section 1.2.2.2 from a distal direction. The flexible separating wall 1.2.3 is integral part with the support body 1.2 and acts as a no-return feature preventing the guide pin 1.1.3 from returning to its start position PI after an injection stroke has at least partially been carried out. Furthermore, the flexible separating wall 1.2.3 guides the movement of the guide pin 1.1.3 within the guide track 1.2.2, so that the guide pin 1.1.3 is prevented to enter an end position PIII from the distal direction but allowed to enter from a proximal direction. The end position PIII is defined by a generally U-shaped indent between the distal and a proximal end of the guide track 1.2.2.

The safety device 1 comprises an essentially cylindrical and hollow outer body 1.3 made from a plastics material with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2 inside the outer body 1.3. The outer body 1.3 comprises three slightly convex outer side walls 1.3.1, wherein each outer side wall 1.3.1 is arranged parallel to one of the first side walls 1.1.2 of the needle shield 1.1. A circumferential and outwardly protruding hand flange 1.3.2 is integrally formed to an exterior surface of the outer body 1.3 close to its distal end.

According to an alternative embodiment of the invention, the needle shield 1.1 comprises a plurality of planar first side walls 1.1.2, the support body 1.2 comprises a plurality of planar second side walls 1.2.1 and the inner sleeve 1.1.5 comprises a plurality of planar third side walls 1.1.5.1. Respectively, the outer side wall 1.3.1 and the inner side wall 1.3.3 of the outer body 1.3 have planar shapes. The needle shield 1.1, the support body 1.2 and the outer body 1.3 have cross-sections extending perpendicular to the central axis A in the shape of polygons and, in particular, in the shape of regular polygons.

The number and shape of the first side walls 1.1.2 of the needle shield 1 corresponds to the number and shape outer side walls 1.3.1, so that the outer body 1.3 may telescope with respect to the needle shield 1.2 during the injection. The number and shape of the outer side walls 1.3.1 may be adapted to provide ergonomic support for the user of the safety device 1. Additionally, the hand flange 1.3.2 provides an ergonomic support for the hand of the user performing a linear injection stroke.

The number and shape of the first side walls 1.1.2 and the outer side walls 1.3.1 may differ from those of the second, the third and the inner side walls 1.2.1, 1.1.5.1, 1.3.3. The shape of inner sleeve 1.1.5, the support body 1.2 corresponds to the number and shape of the inner side walls 1.3.3 of the outer body 1.3. The second, the third and the inner side walls 1.2.1, 1.1.5.1, 1.3.3 are shaped correspondingly, so that a relative rotation between needle shield 1.1, support body 1.2 and outer body 1.3 is avoided. In particular, the outer body 1.3 moves with respect to the support body 1.2 and the needle shield 1.1 in a linear translatory movement.

FIGS. 2A to 2C show exploded views of the injection device D.

FIG. 2A illustrates the arrangement of a spring means 1.4 relative to the support body 1.2. The spring means 1.4 is made from a resilient plastics material like a polymer or an elastomer and comprises three generally L-shaped spring leaves 1.4.1.

In an alternative embodiment of the invention, the spring means 1.4 is arranged with the support body 1.2 as one piece. In particular, the spring means 1.4 may be integral formed to a distal shroud 1.2.4 of the support body 1.2.

FIG. 2B shows one of the spring leaves 1.4.1 arranged relative to the support body 1.2, so that the spring leaf 1.4.1 bears against an inner surface of the distal shroud 1.2.4 of the support body 1.2 in the proximal direction. The distal shroud 1.2.4 comprises a plurality of limiting catches 1.2.4.1 to prevent a translation of the spring leaf 1.4.1 in a direction perpendicular to the central axis A. The spring leaf 1.4.1 bends and is stressed when the needle shield 1.1 is slid with respect to the support body 1.2 from the initial position I in a proximal direction.

FIG. 2C shows an exploded view of the injection device D. Each of the three spring leaves 1.4.1 is oriented at angle relative to each other. Each spring leaf 1.4.1 is arranged adjacent to one of the first side walls 1.1.2 of the needle shield 1.1 in a plane substantially parallel to the first side wall 1.1.2 of the needle shield 1.1. The double-walled outer body 1.3 comprises three outer side walls 1.3.1 and three inner side walls 1.3.3.

Each inner side wall 1.3.3 is arranged parallel to one of the second side walls 1.2.1 of the support body 1.2, so that the support body 1.2 slides into the hollow space formed by the three inner side walls 1.3.3 when the outer body 1.3 is slid with respect to the inner body 1.2 in the distal direction, whereby a rotation of the outer body 1.3 with respect to the support body 1.2 is prevented.

FIG. 3 shows an exploded side view of the injection device D. The inner sleeve 1.1.5 of the needle shield 1.1 is sized to be received in the distal end of the support body 1.2, so that the inner sleeve 1.1.5 apposes each of the three second side walls 1.2.1 of the support body 1.2. When the needle shield 1.1 is slid relative to the support body 1.2 a relative rotation of these parts 1.1, 1.2 is prevented by the inner sleeve 1.1.5 abutting the three second side walls 1.2.1 of the support body 1.2.

Figure 4:
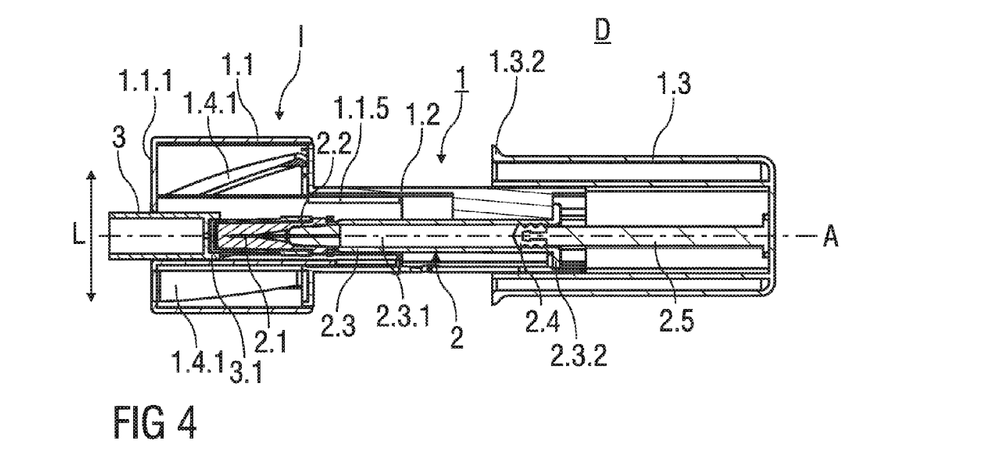
FIG. 4 shows a sectional view of the injection device prior to use.

FIG. 4 shows a sectional view of the injection device D comprising the safety device 1 and the pre-filled syringe 2 prior to use. The pre-filled syringe 2 received within the support body 1.2 comprises the hypodermic needle 2.1 covered by the needle cap 2.2 that is frictionally affixed to a distal end of a barrel 2.3. The barrel 2.3 has an inner cavity 2.3.1 containing a medication. The inner cavity 2.3.1 is in fluid communication with the hypodermic needle 2.1. A proximal end of the inner cavity 2.3.1 is fluid-tightly sealed by a piston 2.4 that is connected to a piston rod 2.5. The piston 2.4 is movable in at least the distal direction by actuating the piston rod 2.5 protruding the barrel 2.3 in the proximal direction. The barrel 2.3 of the pre-filled syringe 2 comprises a barrel collar 2.3.2 that abuts a radial inwardly protruding inner surface of the support body 1.2 at its proximal end affixing the pre-filled syringe 2 to the support body 1.2.

The spring leaves 1.4.1 bear against the distal shroud 1.2.4 in the proximal direction and against an inner surface of the distal end surface 1.1.1 in the distal direction. The spring leaves 1.4.1 bias the needle shield 1.1 with respect to the support body 1.2 in the distal direction.

The pre-filled syringe 2 is retained within the support body 1.2, whereby the hypodermic needle 2.1 protrudes the support body 1.2 in the distal direction. The support body 1.2 may comprise clips that engage the barrel collar 2.3.2 in a snap-lock kind of connection to retain the pre-filled syringe 2 within the support body 1.2.

In the packaged state as shown in FIGS. 1 and 4, the hypodermic needle 2.1 is covered by the needle cap 2.2 that is surrounded by the needle shield 1.1 prior to use of the injection device D. The needle cap 2.2 is preferably at least partially made from a plastics material like rubber. The width of the central opening of the distal end surface 1.1.1 corresponds to an outer diameter of the needle cap 2.2. A needle cap remover 3 is inserted into the central opening of the distal end surface 1.1.1 and protrudes the distal end surface 1.1.1 in a distal direction, so that the user can easily remove the needle cap 2.2 from the pre-filled syringe 2 by pulling the needle cap remover 3 in the distal direction. The needle cap remover 3 comprises clamp means 3.1 that clamp to a distal end of the needle cap 2.2.

Alternatively, the injection device D comprising the safety device 1 with the pre-filled syringe 2 retained therein is shipped and delivered to an end-user with a needle cap remover 3 attached to the distal end of the needle cap 2.2 retained within the safety device 1, so that the needle cap remover 3 protrudes the needle shield 1.1 in the distal direction.

Figure 5:
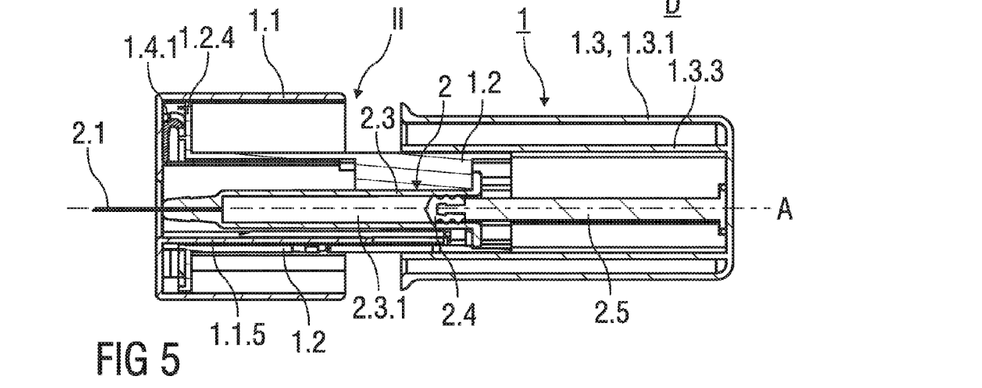
FIG. 5 shows a sectional view of the injection device at the beginning of an injection stroke.

FIG. 5 shows a sectional view of the injection device D at the beginning of the injection stroke delivering a medication beneath the skin of a patient. A proximal end of the piston rod 2.5 abuts the closed proximal end of the outer body 1.3, so that the piston 2.4 is movable in a distal direction by a distal displacement of the outer body 1.3 with respect to the support body 1.2.

Alternatively, the piston rod 2.5 is connected to the outer body 1.3 or integral to the outer body 1.3. This alternative embodiment has additional advantage of a low overall part count, so that manufacturing costs are reduced.

The needle shield 1.1 is in a retracted position II, wherein the needle shield 1.1 is retracted with respect to the initial position I by a axial distance that substantially corresponds the axial length L1. The hypodermic needle 2.1 of the pre-filled syringe 2 is exposed. The hypodermic needle 2.1 distally protrudes the distal end surface 1.1.1 of the needle shield 1.1. When the needle shield 1.1 is in the retracted position II, the spring leaves 1.4.1 reach a maximal deflection length, so that the spring leaves 1.4.1 are maximally bended and stressed.

Figure 6:
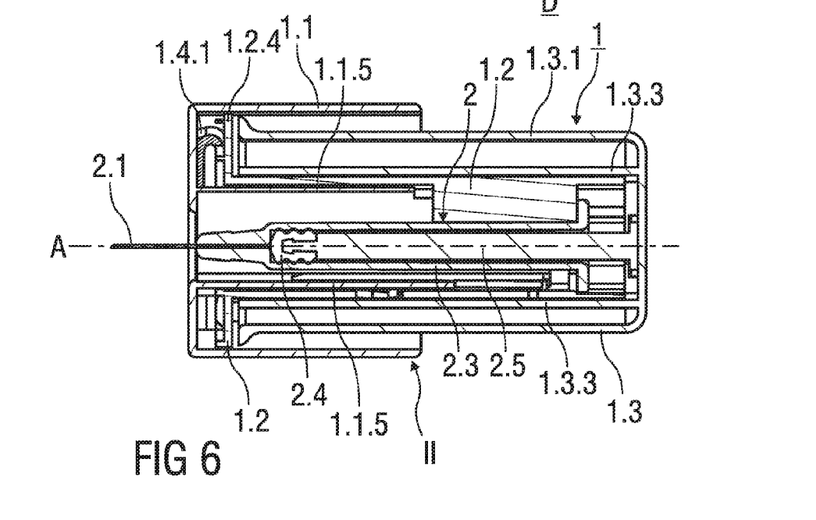
FIG. 6 shows a sectional view of the injection device at the end of an injection stroke.

FIG. 6 shows a sectional view of the injection device D with the safety device 1 at the end of the injection stroke. The needle shield 1.1 is in the retracted position II. The guide pin 1.1.3 that is integral to the needle shield 1.1 is in an intermediate position PII within the guide track 1.2.2 in proximity of a proximal end thereof. The intermediate position PII of the guide pin 1.1.3 within the guide track 1.2.2 corresponds to the retracted position II of the needle shield 1.1.

The outer body 1.3 telescopes with respect to the needle shield 1.1. At the end of the injection stroke, a substantial part of the outer body 1.3 is received inside the needle shield 1.1.

Figure 7:
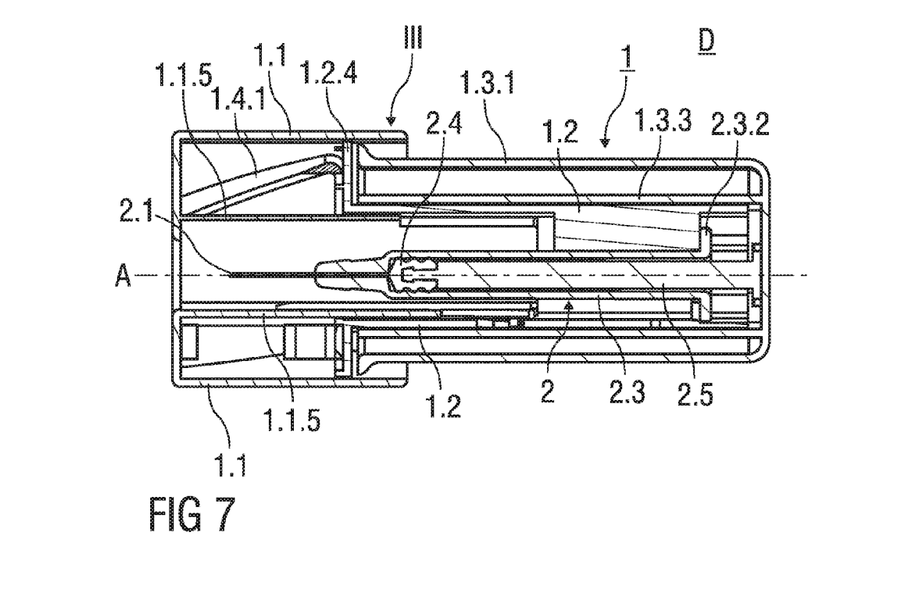
FIG. 7 shows a first sectional view of the injection device after an injection has been performed.

FIG. 7 shows a sectional view of the injection device D with the safety device 1 after the injection of the medication. The needle shield 1.1 is in an advanced position III protruding distally from the support body 1.2, whereas the hypodermic needle 2.1 is surrounded by the needle shield 1.1 to avoid accidental needle stick injuries. The needle shield 1.1 is affixed to the advanced position III by the guide pin 1.1.3 being retained in the end position PIII.

Figure 8:
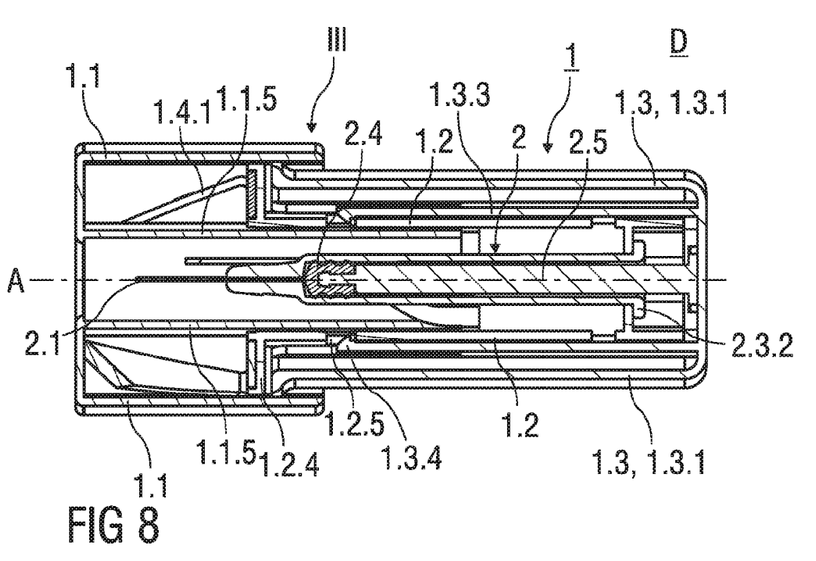
FIG. 8 shows a second sectional view of the injection device after an injection has been performed.

FIG. 8 shows a sectional view of the safety device 1, whereas the plane section shown extends essentially perpendicular to the cross-section shown in FIG. 7. The piston 2.4 is fully depressed inside the barrel 2.3 of the pre-filled syringe 2. The support body 1.2 is received within the outer body 1.3 and locked to it, so that a re-usage of the safety device 1 is prevented. An inwardly protruding locking catch 1.3.3 formed to an inner surface of the outer body 1.3 latches to a corresponding locking recess 1.2.4 formed into the support body 1.2 to irreversibly lock the support body 1.2 with respect to the outer body 1.3.

FIGS. 9A to 9F show details of the guide track 1.2.2 formed into the support body 1.2 and the movement of the guide pin 1.1.3 within the guide track 1.2.2 during use of the safety device 1.

Figure 9A:
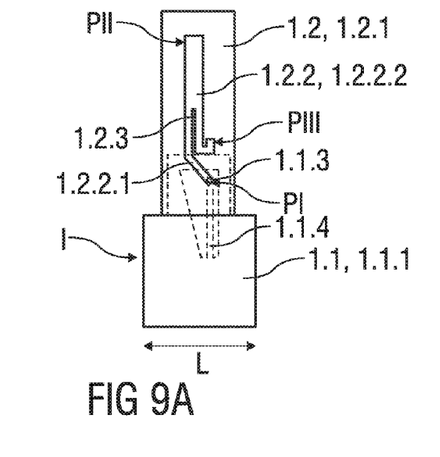
FIGS. 9A to 9F show details of a guide track accommodating a guide pin and the movement of the guide pin within the guide track during the injection.

As shown in FIG. 9A, the guide pin 1.1.3 is retained prior to the injection in the start position PI at the distal end of the inclined section 1.2.2.1 of the guide track 1.2.2, affixing the needle shield 1.1 to the initial position I. In the initial position I, the hypodermic needle 2.1 is surrounded by the needle shield 1.1.

The injection is carried out by orientating the central axis A essentially perpendicular to the skin of the patient, whereas the distal end surface 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out the injection stroke.

Figure 9B:
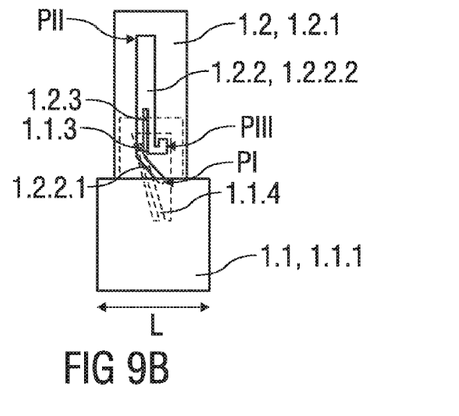

The injection is carried out in stages. In a first stage, the needle shield 1.1 is pushed inside the support body 1.2 in the proximal direction against the biasing force exerted upon the needle shield 1.1 by the spring leaves 1.4.1. As illustrated in FIG. 9A and FIG. 9B, the guide pin 1.1.3 leaves its start position PI and moves along the inclined section 1.2.2.1 of the guide track 1.2.2. As the inclined section 1.2.2.1 is oriented at an acute angle relative to the central axis A, the movement of the guide pin 1.1.3 causes the flexible arm 1.1.4 to become laterally deflected and stressed, so that the guide pin 1.1.3 is biased in a lateral direction L.

Figure 9C:
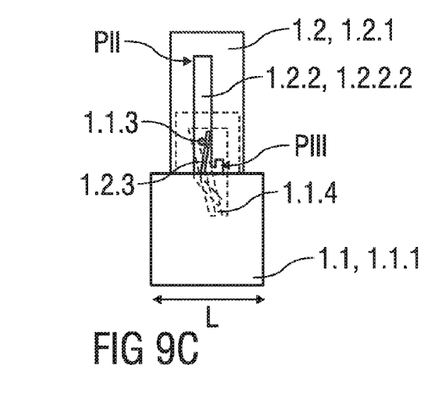

The guide pin 1.1.3 travels further along the guide track 1.2.2 in the proximal direction. As shown in FIG. 9C, the guide pin 1.1.3 enters the widened section 1.2.2.2 of the guide track 1.2.2 and abuts the flexible separating wall 1.2.3 in the lateral direction L. The flexible separating wall 1.2.3 is laterally deflected by a force exerted upon the flexible separating wall 1.2.3 by the stressed flexible arm 1.1.4. The elasticity of the flexible separating wall 1.2.3 is adapted to correspond to the elasticity of the flexible arm 1.1.4, so that the flexible separating wall 1.2.3 is deflectable by the deflected and stressed flexible arm 1.1.4.

The flexible separating wall 1.2.3 prevents the guide pin 1.1.3 from entering the end position PIII as the guide pin 1.1.3 enters the widened section 1.2.2.2 from the distal direction.

Figure 9D:
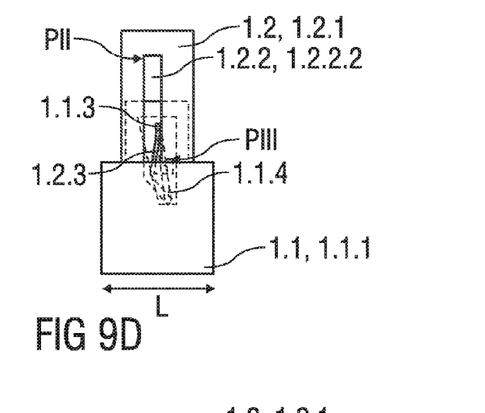

The guide pin 1.1.3 moves further proximally towards an intermediate position PII and reaches a proximal end of the flexible separating wall 1.2.3, as illustrated in FIG. 9D. At this point, the safety features of the safety device 1 are activated, as the flexible separating wall 1.2.3 relaxes and snaps back into its rest position substantially parallel to the central axis A. From now on, the end position PIII is accessible for the guide pin 1.1.3 to enter whereas the guide pin 1.1.3 is prevented to re-enter the start position PI. A subsequent removal of the safety device 1 causes the needle shield 1.1 and the guide pin 1.1.3 to advance distally, so that the needle shield 1.1 surrounds the hypodermic needle 2.1 of the pre-filled syringe in an advanced position III. The needle shield 1.1 is firmly retained in the advanced position III by the guide pin 1.1.3 being retained in the U-shaped indent of the guide track 1.2.2 defining the end position PIII, whereby a re-usage of the injection device D and/or the safety device 1 is prevented.

The flexible separating wall 1.2.3 has an axial dimension extending parallel to the central axis A and into the widened section 1.2.2.2 of the guide track 1.2.2. The axial dimension defines a minimal axial distance that the needle shield 1.1 has to be moved with respect to the support body 1.2 before the advanced position III is accessible for the needle shield 1.1 to enter. At the same time the safety features that prevent a re-usage of the safety device 1 are activated. Thus, an unintentional activation of the safety features of the safety device 1 is avoided, when the needle shield 1.1 is accidentally pushed distally by a length that is smaller than the minimal axial distance.

The safety device 1 generates an audible feedback indicating the activation of the safety features. The audible feedback can be generated by the flexible separating wall 1.2.3 snapping back into its rest position substantially parallel to the central axis A when the needle shield 1.1 is distally moved with respect to the support body 1.2 by a length that exceeds the minimal axial distance.

In order to inject the medication, the needle shield 1.1 is moved further in the proximal direction until it reaches the retracted position III illustrated in FIG. 3, whereby the guide pin 1.1.3 is retained within the guide track 1.2.2 in the intermediate position PII. The spring leaves 1.4.1 are maximally bent and fully stressed to bias the needle shield 1.1 with respect to the support body 1.2 in the distal direction. The user performing the injection presses the distal end surface 1.1.1 against the biasing force towards the skin surface of the patient, so that the hypodermic needle 2.1 penetrates the skin of the patient and the medication contained in the inner cavity 2.3.1 can be injected in the following second stage of the injection.

In the second stage, the outer body 1.3 moves with respect to the support body 1.1 in the distal direction. Simultaneously, the piston rod 2.5 interacting with the outer body 1.3 is actuated to move the piston 2.4 in the distal direction, whereby the medication contained in the inner cavity 2.3.1 is delivered through the hypodermic needle 2.1 and beneath the skin of the patient.

At the end of the injection stroke, the inwardly protruding locking catch 1.3.4 formed to an inner surface of the outer body 1.3 latches to the corresponding locking recess 1.2.5 formed into the support body 1.2 to irreversibly lock the support body 1.2 with respect to the outer body 1.3. As the support body 1.2 is substantially received within the outer body 1.3 at the end of the injection stroke, the guide pin 1.1.3 and the guide track 1.2.2 is inaccessible from outside. This prevents a user to tamper with the guide pin 1.1.3 and the guide track 1.2.2 retaining the needle shield 1.1 in the advanced position III, so that a re-use of the safety device 1 is prevented.

Figure 9E:
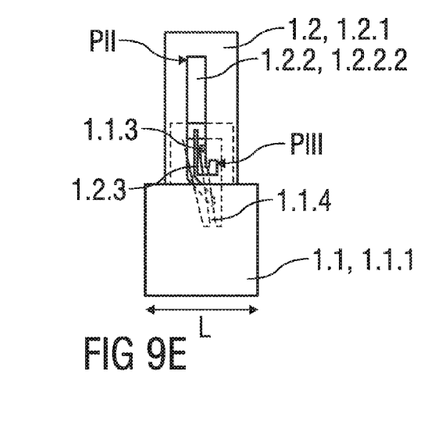

The injection device D comprising the safety device 1 with the pre-filled syringe 2 received therein is removed from the injection site. The needle shield 1.1 immediately moves distally towards the advanced position III by the action of the relaxing spring leaves 1.4.1. As indicated in FIG. 9E, the guide pin 1.1.3 jointly moves with the needle shield 1.1 distally, whereby the guide pin 1.1.3 is guided by the flexible separating wall 1.2.3 towards the end position PIII.

Figure 9F:
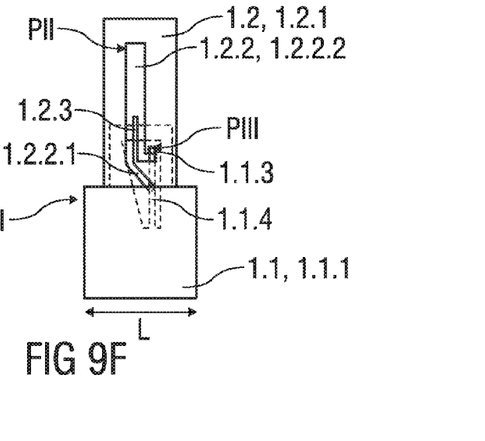

As indicated in FIG. 9F, the guide pin 1.1.3 enters the U-shaped indent defining the end position PIII of the guide track 1.2.2, whereby the flexible arm 1.1.4 relaxes to move the guide pin 1.1.3 laterally towards the end position PIII.

The guide pin 1.1.3 is firmly retained in the end position PIII, as the guide pin 1.1.3 abuts the U-shaped indent in the distal and in the lateral direction L. The flexible arm 1.1.4 is in the rest position, so that the guide pin 1.1.3 is laterally non-biased in the end position PIII. A lateral movement of the guide pin 1.1.3 is prevented by the form of the U-shaped indent of the guide track 1.2.2 at the end position PIII and by the flexible arm 1.1.4. Thus, the guide pin 1.1.3 in the end position PIII irreversibly locks the needle shield 1.1 into the advanced position III after a single use of the safety device 1.

In one embodiment of the invention, the hypodermic needle 2.1 is hidden from the view of the patient throughout the injection.

The safety device 1 presented herein provides a simple mechanism to avoid needle stick injuries. The injection is carried out by a simple linear movement of the outer body 1.3 towards the skin of the patient, whereby the safety features that provide needle safety and prevent re-usage of the safety device 1 are automatically activated. The triangular design of the safety device 1 differs from typical designs of safety devices 1 for pre-filled syringes 2 to alleviate a possible fear of injections. The safety device 1, including the spring means 1.4, is exclusively made from plastics materials.

The invention claimed is:

1. A safety device for a pre-filled syringe, comprising:
a hollow support body suitable for substantially containing and retaining the pre-filled syringe therein, such that a hypodermic needle of the pre-filled syringe protrudes from the support body in a distal direction;
a hollow needle shield that shields the hypodermic needle of the pre-filled syringe contained within the hollow support body, wherein the needle shield comprises a plurality of substantially planar or convex side walls;
a double-walled outer body comprising a plurality of outer side walls, the outer body being configured to telescope with respect to the needle shield, and each outer side wall being arranged parallel to one of the side walls of the needle shield;
a spring made from a resilient plastics material,
wherein the needle shield is telescoped with the support body,
wherein the spring is arranged between the needle shield and the support body and biases the needle shield in the distal direction,
wherein the spring comprises a plurality of generally L-shaped resilient spring leaves, each of the spring leaves being operably connected to a distal end wall of the needle shield and to a distal shroud of the support body to bias the distal end wall and the distal shroud away from each other, and
wherein the distal shroud comprises a plurality of catches to inhibit translation of the spring leaves, each of the catches limiting translation of a corresponding spring leaf.

2. The safety device according to claim 1, wherein the needle shield comprises an axial length that substantially corresponds to maximal spring deflection of the spring.

3. The safety device according to claim 1, wherein all side walls of the needle shield have a same width.

4. The safety device according to claim 1, wherein the spring leaves are oriented relative to each other at an angle, and each of the spring leaves is arranged adjacent to one of the side walls of the needle shield in a plane substantially parallel to the side wall of the needle shield.

5. The safety device according to claim 1, wherein: the support body comprises a plurality of substantially planar or convex side walls, and
an inner sleeve of the needle shield comprises a plurality of substantially planar or convex side walls, each side wall of the needle sleeve being arranged parallel to one of the side walls of the support body.

6. The safety device according to claim 5, wherein:
all side walls of the support body have a same width, and
all side walls of the inner sleeve have a same width.

7. The safety device according to claim 5, further comprising at least one flexible arm formed to the inner sleeve, the flexible arm being deflectable in a lateral direction perpendicular to a central axis and comprising a guide pin that protrudes in a radial direction.

8. The safety device according to claim 7, further comprising a guide track formed into at least one of the side walls of the support body, wherein the guide pin protrudes into the guide track and is configured to interact with the guide track to retain the needle shield in an initial position and in an advanced position, the guide pin being further configured to interact with the guide track to guide the movement of the needle shield between the initial position, a retracted position and the advanced position.

9. The safety device according to claim 5, wherein the double-walled outer body comprises a plurality of inner side walls,
wherein each inner side wall is arranged parallel to one of the side walls of the support body, and
wherein the outer body is configured to telescope with respect to the support body.

10. The safety device according to claim 9, wherein the support body is substantially received within the outer body at the end of an injection stroke, whereby the support body is locked relative to the outer body.

11. An injection device comprising:
a pre-filled syringe comprising a hypodermic needle; and
a safety device comprising
a hollow support body suitable for substantially containing and retaining the pre-filled syringe therein, such that the hypodermic needle of the pre-filled syringe protrudes from the support body in a distal direction;
a hollow needle shield that shields the hypodermic needle of the pre-filled syringe contained within the hollow support body, wherein the needle shield comprises a plurality of substantially planar or convex side walls;
a double-walled outer body comprising a plurality of outer side walls, the outer body being configured to telescope with respect to the needle shield, and each outer side wall being arranged parallel to one of the side walls of the needle shield;
a spring made from a resilient plastics material,
wherein the needle shield is telescoped with the support body,
wherein the spring is arranged between the needle shield and the support body and biases the needle shield in the distal direction,
wherein the spring comprises a plurality of generally L-shaped resilient spring leaves, each of the spring leaves being operably connected to a distal end wall of the needle shield and to a distal shroud of the support body to bias the distal end wall and the distal shroud away from each other, and
wherein the distal shroud comprises a plurality of catches to inhibit translation of the spring leaves, each of the catches limiting translation of a corresponding spring leaf.

12. The injection device according to claim 11, wherein:
the spring leaves are oriented relative to each other at an angle, and
each of the spring leaves is arranged adjacent to one of the side walls of the needle shield in a plane substantially parallel the side wall of the needle shield.

13. The injection device of claim 11, wherein the hypodermic needle is integral to the pre-filled syringe.

14. A safety device for a pre-filled syringe, comprising:
a hollow support body suitable for substantially containing and retaining the pre-filled syringe therein, such that a hypodermic needle of the pre-filled syringe protrudes from the support body in a distal direction, the support body comprising a plurality of substantially planar or convex side walls;
a hollow needle shield that shields the hypodermic needle of the pre-filled syringe contained within the hollow support body, the hollow needle shield comprising an inner sleeve having a plurality of substantially planar or convex side walls, each side wall of the needle shield being arranged parallel to one of the side walls of the support body;
a double-walled outer body comprising a plurality of inner side walls, the outer body being configured to telescope with respect to the support body, and each inner side wall being arranged parallel to one of the side walls of the support body, and
wherein a spring made from a resilient plastics material,
wherein the needle shield is telescoped with the support body,
wherein the spring is arranged between the needle shield and the support body and biases the needle shield in the distal direction,
wherein the spring comprises a plurality of generally L-shaped resilient spring leaves, each of the spring leaves being operably connected to a distal end wall of the needle shield and to a distal shroud of the support body to bias the distal end wall and the distal shroud away from each other, and
wherein the distal shroud comprises a plurality of catches to inhibit translation of the spring leaves, each of the catches limiting translation of a corresponding spring leaf.

* * * * *

UNITED STATES PATENT AND TRADEMARK OFFICE
CERTIFICATE OF CORRECTION

| | | |
|---|---|---|
| PATENT NO. | : 9,649,453 B2 | Page 1 of 1 |
| APPLICATION NO. | : 13/880518 | |
| DATED | : May 16, 2017 | |
| INVENTOR(S) | : Gareth Roberts, Chris Ward and Matthew Ekman | |

It is certified that error appears in the above-identified patent and that said Letters Patent is hereby corrected as shown below:

In Column 12, Line 55, in Claim 5, delete "needle" and insert --inner--

In Column 13, Line 36, in Claim 11, delete ";" and insert --; and--

In Column 14, Line 31, in Claim 14, delete ", and" and insert --; and--

In Column 14, Line 32, in Claim 14, delete "wherein"

Signed and Sealed this
Eighth Day of August, 2017

Joseph Matal
*Performing the Functions and Duties of the*
*Under Secretary of Commerce for Intellectual Property and*
*Director of the United States Patent and Trademark Office*